US006291488B1

(12) United States Patent
Gutteridge et al.

(10) Patent No.: US 6,291,488 B1
(45) Date of Patent: *Sep. 18, 2001

(54) PREVENTING PROTOZOAL INFECTIONS

(75) Inventors: Winston Edward Gutteridge; David Brian Ashton Hutchinson; Victoria Susan Latter; Mary Pudney, all of Beckenham (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/678,485

(22) Filed: Oct. 4, 2000

Related U.S. Application Data

(62) Division of application No. 09/409,871, filed on Oct. 1, 1999, now Pat. No. 6,166,046, which is a division of application No. 08/962,273, filed on Oct. 31, 1997, now Pat. No. 5,998,449, which is a continuation of application No. 08/436,285, filed as application No. PCT/GB93/02425 on Nov. 25, 1993, now abandoned.

(30) Foreign Application Priority Data

Nov. 26, 1992 (GB) .................................................. 9224739

(51) Int. Cl.$^7$ .......................... A61K 31/15; A61K 31/155
(52) U.S. Cl. .......................... 514/350; 514/565; 514/682; 514/895
(58) Field of Search .................................. 514/350, 565, 514/682, 895; 552/298, 299; 564/234

(56) References Cited

U.S. PATENT DOCUMENTS

| | | |
|---|---|---|
| 2,533,648 | 5/1950 | Fieser et al. . |
| 3,347,830 | 10/1967 | Rogers . |
| 3,367,742 | 2/1968 | Sarett . |
| 3,674,872 | 7/1972 | Rheimer et al. . |
| 4,981,874 | 1/1991 | Latter et al. . |
| 5,053,418 | 10/1991 | Latter et al. . |
| 5,053,432 | 10/1991 | Hudson et al. . |
| 5,206,268 | 4/1993 | Latter et al. . |
| 5,310,762 | 5/1994 | Latter et al. . |
| 5,529,994 * | 6/1996 | Remington et al. .................. 514/183 |
| 5,747,476 * | 5/1998 | Russell et al. ........................ 514/275 |
| 5,840,893 * | 11/1998 | Bukrinsky et al. .................. 544/329 |
| 5,998,449 * | 12/1999 | Gutteridge et al. .................. 514/350 |
| 6,018,080 * | 1/2000 | Dearn .................................. 568/309 |
| 6,107,316 * | 8/2000 | Young et al. ........................ 514/359 |
| 6,114,393 * | 9/2000 | Lang et al. .......................... 514/634 |
| 6,166,046 * | 12/2000 | Gutteridge et al. .................. 514/350 |

FOREIGN PATENT DOCUMENTS

| | | |
|---|---|---|
| 0 002 228 B1 | 6/1979 | (EP) . |
| 0 077 550 B1 | 4/1983 | (EP) . |
| 0 077 551 A2 | 4/1983 | (EP) . |
| 0 123 238 A3 | 10/1984 | (EP) . |
| 0 123 239 A2 | 10/1984 | (EP) . |
| A 0123238 A2 | 10/1984 | (EP) . |
| 0 362 996 A2 | 4/1990 | (EP) . |
| 0 401 875 A3 | 12/1990 | (EP) . |
| 0 537 947 A1 | 4/1993 | (EP) . |
| 1 141 735 | 1/1969 | (GB) . |
| 1 268 316 | 3/1972 | (GB) . |
| 1 533 424 | 9/1979 | (GB) . |
| WO 91/04021 | 4/1991 | (WO) . |
| WO 91/0550 | 5/1991 | (WO) . |
| 99/04784 * | 2/1999 | (WO) . |
| 0061133 * | 10/2000 | (WO) . |

OTHER PUBLICATIONS

Parasitol. Today, vol. 8, No. 8, pp 252–255, C.P.J. Ash "Fourth malaria meeting" Aug. 1992.
Parasitol. Today, vol. 9, No. 2, pp. 66–68, A.T. Hudson "Atovaquone—a novel broad–spectrum anti–infective drug" 2/93.
Abstract and Poster by M. Pudney et al VIII International Congress of Protozoology, Jul. 10–17, Tsukuba, Japan 1992.
Wofsy, pp 377–401, Chapter 36, 1986.
Fieser et al vol. 70, pp 3156–3165, 1948.
Hughs, Parasitology Today, vol. 3, No. 11, pp. 332–335, 1887.
Parsons, 10 pages, issued Aug. 7, 1989.
Discriminant Analysis and Structure–Activity Relationships 1. Naphthoquinone; J. Med. Chem. vol. 21; No. 4, 1978 pp 369–374.
Role of the Naphthoquinone Moiety in the Biological Activities of Sakyomicin A: J. Antibiot. vol. 39; No. 4, 1986; pp 557–563.
Inhibition of Thioredoxin Reductase (E.C. 1.6.4.5) by Antitumor Quinones; Free Rad. Res. Commun. vol. 8; No. 4–6; 1990; pp 365–372.
Shargel et al Applied Biopharmaceutics and Pharmacokinetics, $2^{nd}$ Edition Appleton–Century–Crofts, 1985 Role of the Naphthoquinone Moiety in the Biological Activities of Sakyomicin A.J. Antibiol/vol. 39, No. 4 1986 pp. 557–563.
Inhibition of Thioredoxin Reductase (E.C. 1645) Antitumor Quinones, Free Rad. Res. Commun. vol. 46, 1990 pp 365–372.
Atovaquone in Phase II trials in Thailand R & D Focus Drug News Feb. 24, 1992 DrugnL Accession No. 92:133.

* cited by examiner

*Primary Examiner*—Robert H. Harrison
(74) *Attorney, Agent, or Firm*—Nixon & Vanderhye

(57) ABSTRACT

The invention relates to combinations of atovaquone and proguanil, their use in the treatment and prophylaxis of parasitic infections such as protozoal parasitic infections, e.g., malaria and toxoplasmosis, and infections caused by *P. carinii* and their use in the manufacture of medicaments for the treatment and/or prophylaxis of such infections. The combinations can conveniently be administered in a single pharmaceutical formulation. Preferably, atovaquone and proguanil are administered in a potentiating ratio so that they act in synergy.

5 Claims, No Drawings

PREVENTING PROTOZOAL INFECTIONS

This is a division of application Ser. No. 09/409,871, filed Oct. 1, 1999, now U.S. Pat. No. 6,166,046 which is a division of 08/962,273 filed Oct. 31, 1997 now U.S. Pat. No. 5,998,449 which is a continuation of 08/436,285, filed May 15, 1995, now abandoned, which is the U.S. national stage of PCT/GB92/02425 filed Nov. 25, 1993the entire content of which us hereby incorporated by reference in this application.

The present invention relates to synergistic combinations of 2-[4-(4-chlorophenyl)cyclohexyl]-3-hydroxy-1,4-naphthoquinone (atovaquone) and proguanil which have anti-parasitic activity. More particularly, the invention is concerned with pharmaceutical compositions containing said combinations, their use in the treatment of protozoal parasitic infections such as malaria and toxoplasmosis and their use in the treatment of infections caused by *Pneumocystis carinii*.

The compound 2-[4-(4-chlorophenyl)cyclohexyl]-3-hydroxy- 1,4-naphthoquinone (atovaquone) has previously been disclosed, for example in European Patent No. 123,238 which relates to 2-substituted-3-hydroxy-1,4-naphthoquinone of formula (I)

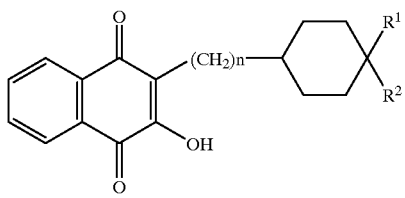

(I)

wherein either $R^1$ is hydrogen and $R^2$ is selected from $C_{1-6}$ alkoxy, aralkoxy, $C_{1-6}$ alkyl-$C_{1-6}$ alkoxy, phenyl substituted by one or two groups selected from halogen and $C_{1-6}$ alkyl, halogen and perhalo-$C_{1-6}$ alkyl or $R^1$ and $R^2$ are both $C_{1-6}$ alkyl or phenyl, and n is zero or 1, and physiologically acceptable salts thereof. The compounds are said to have antiprotozoal activity. Specifically, compounds of formula. (I) wherein n is zero are said to be active against the human malaria parasite *Plasmodium falciparum* and also against Eimeria species such as *E. tenella* and *E. acervulinam* which are causative organisms of *coccidiosis* and compounds of formula where n is 1 are said to be active against protozoa of the genus Theileria, in particular *T. annulata* or *T. parva*. Amongst the compounds specifically named and exemplified is the compound of formula (I) wherein n is zero, $R^1$ hydrogen and $R^1$ is 4-chlorophenyl, i.e. atovaquone.

Proguanil is a well-known drug for prophylaxis, but not treatment, of malaria. It is one of the safest antimalarial drugs and may be given to young children and pregnant women. However resistance of *P. falciparum* to proguanil has appeared particularly in South East Asia, and is an increasing problem.

In order to combat drug resistance it is becoming standard practice to use combinations of more than one antimalarial, either simultaneously or sequentially. However, many such combinations are antagonistic, resulting in less effective treatment and the dosage regimens are often complicated, increasing the likelihood of patients failing to complete the treatment. Accordingly, it was an object of the present invention to provide a combination of antimalarial drugs which was not antagonistic and which did not require a complex dosing regimen.

It has now surprisingly, been found that by combining, either concomitantly or sequentially, atovaquone, represented in this specification by formula (II):

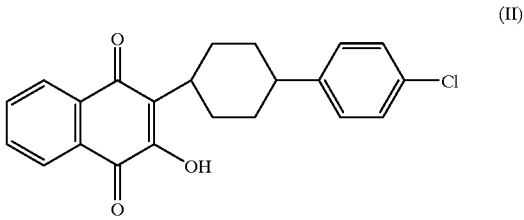

(II)

and proguanil, potentiation of antiparasitic and particularly antimalarial activity is achieved. Furthermore a potentiating combination of the compound of formula (II) and proguanil can be simply presented in a single pharmaceutical formulation.

In a first aspect, the present invention provides a method for the treatment and/or prophylaxis of a protozoal parasitic infection, e.g. malaria or toxoplasmosis, or an infection caused by *P.Carinii* in mammals, including humans, which comprises administering an effective amount of atovaquone or a physiologically acceptable salt thereof and concomitantly or sequentially administering an effective amount of proguanil.

In a second aspect, the present invention provides atovaquone for use in the manufacture of a medicament, for administration either concomitantly or sequentially with proguanil, for treatment and/or prophylaxis of a protozoal parasitic infection, e.g. malaria or toxoplasmosis or an caused by *P. carinii*, in mammals, including humans.

Preferably the compound of formula (B) and proguanil are administered concomitantly. Most preferably the compound of formula (II) and proguanil are administered in a potentiating ratio.

Thus, according to a further aspect of the present invention, there is provided a combination of atovaquone, or a pathologically acceptable salt thereof, and proguanil wherein atovaquone, or its salt, and proguanil are present in a potentiating ratio.

The term 'potentiating ratio' is used herein to indicate that atovaquone and proguanil are present in a ratio such that the antiparasitic activity of the combination is greater than that of either atovaquone or proguanil alone or of the additive activity that would be predicted for the combination based on the activities of the individual components. Thus the individual components act synergistically in combination provided they are present in a potentiating ratio.

A potentiating ratio, which may be successfully used to treat malaria, including hydroxynaphthoquinone resistant strains of malaria is in the range 1:0.1–1:100 of proguanil: atovaquone. Suitably, the potentiating ratio is in the range 1:0.2–1.10.

A particularly preferred potentiating ratio is in the range 1:1–1:3.

The present invention also provides in another aspect a method for the treatment and/or prophylaxis of malaria in mammals, including humans, which comprises administering an effective amount of a combination of atovaquone, or a physiologically acceptable salt thereof and proguanil.

The hydroxyl group of atovaquone may form salts with appropriate bases, and physiologically acceptable salts of atovaquone include inorganic base salts such as alkali metal (e.g. sodium and potassium) salts and alkaline earth metal (e.g. calcium salts: organic base salts e.g. phenylethylbenzylamine, dibenzylethylenediamine, ethanolamine and diethanolamone salts: and amino acid salts e.g. lysine and arginine.

It will be appreciated that the compound of formula (II) may exist as the cis or trans isomer, that is to say that the cyclohexyl ring any be cis or trans substituted by the naphthoquinone nucleus and the chlorophenyl group. Both cis and trans isomers and mixtures thereof in any ratio may be used in accordance with the present invention. In general mien the compound is in the form of a mixture of isomers the trans isomer will be present in an amount of about 50% or will be the predominant isomer but the use of mixtures in which the cis isomer predominates is also included within the scope of the invention. The specific ratio of isomers may be varied as required; typical mixtures include those in which cis/trans isomer ratio is about 1:1,40:60 and 5:95. For use according to the present invention the trans isomer of the compound of formula (II), or a mixture of its cis and trans isomers containing at least 95% e.g. 99% of the trans isomer, is preferred.

The compound of formula (II) may also exist in a tautomeric form in which the hydroxyl group donates its proton to one of the one groups and the use of such tautomeric forms is included within the scope of this invention. However, it is believed that the stable form is that shown in formula (II).

The amount of a combination of atovaquone and proguanil required to be effective as an antiparasitic agent will, of course, vary and is ultimately at the discretion of the medical or veterinary practitioner. The factors to be considered include the route of administration and nature of the formulation, the mammal's bodyweight, age and general condition and the nature and severity of the disease to be treated. In general, a suitable effective dose for administration to man for treatment of malaria is in the range of 2.0 mg to 30 mg of proguanil per kilogram bodyweight per day and 0.5 mg to 30 mg of atovaquone per kilogram bodyweight per day, for example from 3 to 20 mg/kg/day of proguanil and 1 to 20 mg/kg/day of atovaquone, particularly 5 to 15 mg/kg/day of proguanil and 3 to 15 mg/kg/day of atovaquone.

At suitable effective dose for administration to man for prophylaxis of malaria is in the range of from 3 to 20 mg per kilogram bodyweight per week of each of proguanil and atovaquone for example from 6 mg/kg/week to 10 mg/kg/week of each of proguanil and atovaquone.

It should be understood that the dosages referred to above are calculated in terms of the drip per se.

For use according to the present invention the combination of atovaquone and proguanil is preferably Presented as a pharmaceutical formulation.

Pharmaceutical formulations comprise the active ingredients (that is, the combination of atovaquone and proguanil) together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

Accordingly, the present invention provides a pharmaceutical formulation comprising a combination of atovaquone and proguanil in association with one or more pharmaceutically acceptable carriers therefor.

The present invention further provides a process for the preparation of a pharmaceutical formulation which process comprises bringing into association a combination of atovaquone and proguanil with one or more pharmaceutically acceptable carriers therefor.

The combination of atovaquone and proguanil may conveniently be presented as a pharmaceutical formulation in unit dosage form. A convenient, unit dose formulation contains the active ingredients in amounts of from 10 mg to 3 g each, e.g. 50 mg to 3 g each. Typical unit doses may contain for example 500 mg of atovaquone and 200 mg of proguanil or 500 mg of atovaquone and 500 mg of proguanil.

Pharmaceutical formulation include those suitable for oral, topical (including dermal,buccal and sublingual),rectal and parenteral (including subcutaneous, intradermal, intramuscular and intravenous), administration as well as administration by naso-gastric tube. The formulation may, where appropriate, be conveniently presented in discrete dosage units and may be prepared by any of the methods well known in the art of pharmacy. All methods include the step of bringing into association the active ingredients with liquid carriers or finely divided solid carriers or both and then, if necessary, shaping the product, into the desired formulation.

Pharmaceutical formulations suitable for oral administration wherein the carrier is a solid are most preferably preserved as unit dose formulations such as boluses, capsules or tablets each containing a predetermined amount of the active ingredients. A tablet may be made by compression or moulding, optionally with one or more accessory ingredients. Compressed tablets may be prepared by compressing in a suitable machines the active compounds in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredients, either alone or in admixture with one or more accessory ingredients, into the capsule shells and then sealing them in the usual manner. Cachets are analogous to capsules wherein the active ingredients together with any accessory ingredient(s) are sealed in a rice paper envelope. The combination of the compound of formula (II) and proguanil may also be formulated as dispersible granules, which, may, for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredients are formulated in an appropriate release—controlling matrix or are coated with a suitable release—controlling film. Such formulations may be particularly convenient for prophylactic use.

The active ingredients may also be formulated as a solution or suspension suitable for administration via a naso-gastric tube.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Pharmaceutical formulations suitable for parenteral administration include sterile solutions or suspensions of the active combination in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredients may be in powder form which are constituted with a suitable vehicle, such as sterile, pyrogen-free water, before use.

The combination of atovaquone and proguanil may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate one or more additional carrier ingredients such as diluents, buffers, flavouring agents, binders surface active agents, thickeners, lubricants, preservatives (including anti-oxidants and the like, and substances included for the purpose of rendering the formulation isotonic with the blood of the intended recipient.

Compositions suitable for veterinary use include those adapted for oral, parenteral, and intrarumenal administration.

Methods for preparing atovaquone are described in EP 123,238, and one specific method is illustrated in Example 1.

EXAMPLE 1

2-[trans-4-(4-Chlorophenyl)cyclohexane]-3-hydroxy-1,4-naphthoquinone a) 4-(4-Chlorophenyl)cyclohexane-1-carboxylic Acid Acetyl chloride (30 g) and finely powdered aluminum chloride (60 g) were stirred together in carbon disulphide (120 ml) and then cooled to −50° C. in a $CO_2$/oxitol bath. Cyclohexene (30 g), previously cooled to −50° C., was added dropwise during 10 minutes while maintaining the temperature of the reaction mixture at below −20° C. The mixture was stirred at −50° C. for a further 60 minutes and the solvent then decanted to leave a gummy orange complex. A little chlorobenzene was added as the material warmed to ambient temperature the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodium hydroxide and water dried over anhydrous sodium sulphate and evaporated to dryness. The product was distilled in vacuo, the fraction boiling at 140–154° C. (0.1 mm Hg) collected diluted with an equal volume of petroleum ether (40–60), cooled to −6° C. and a continuous stream of nitrogen gas bubbled through, and the separated colourless solid recovered.

Bromine (2.8 ml) was added to a solution of sodium hydroxide (6.2 g) in water (42 ml) at 0° C. The above-obtained substituted kexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite added to destroy excess hypobromite, the mixture cooled and then acidified to give a colourless solid. The solid was filtered off, washed with water, dried and recrystallised from ethanol to give 4-(4-chlorophenyl) cyclohexane- 1-carboxylic acid, m.p. 254–256° C.

b) 2-[4-(4-chlorophenyl)cyclohexyl]-3-chloro-1,4-naphthoquinone

A mixture of 2-chloro-1,4-naphthoquinone (3.95 g, 0.02 mol), 4-(4-chlorophenyl)cyclohexane-1-carboxylic acid (4.9 g, 0.02 mol) and powdered silver nitrate (1.05 g, 0.0062 mol) was heated to reflux with vigorous stirring in 40 ml of acetonitrile. A solution of ammonium persulphate (12.0 g, 0.0525 mol) in 50 ml of water was added dropwise over 1 hour. The mixture was refluxed for 3 hours then cooled in ice for 30 mins, after which it was filtered and the residual sticky solid extracted twice with boiling chloroform to remove inorganic material. The chloroform was removed by evaporation to leave a yellow-brown solid (ca 2.7 g). This was dissolved in 40 ml of boiling acetonitrile; a little insoluble material was removed by filtration. On cooling the title compound separated as yellow crystals, (550 mg) m.p. 172–175° C.

NMR dH($\delta_6$-DMSO) 8.05 (2H, mult., β-naphth), 7.85 (2H, mult., a-naphth), 7.30 (4H, s., PhH), 3.30 (1H br.t., CH), 2.67 (1H, br.t., CH), 1.2–2.4 (8H mult., 4x$CH_2$).

2-[4-(4-chlorophenyl)cyclonexyl]-3-hydroxy-1,4-naphthoquinone

The product of stage (b) was suspended in 10 ml of boiling methanol and 0.55 g of potassium hydroxide in 5.5 ml of water was added dropwise over 15 mins. The mixture was refluxed until a dark red solution formed (after ca. 6 hrs) when 2 ml of concentrated hydrochloric acid was cautiously added dropwise. The mixture was cooled and filtered, and the solid residue washed thoroughly with water. The water washings were re-acidified and filtered. The combined solid residues (500 mg) mp 200–209°, were recrystallised from a acetonitrile to give the title product as the trans-isomer (300 mg) m.p. 216–219° C.

EXAMPLE 2

The following examples illustrate conventional pharmaceutical formulations which may be employed in accordance with the present invention:

| | | |
|---|---|---|
| A. | Film-coated tablet | |
| | Core: | |
| | Compound of Example 1 | 500 mg |
| | Proguanil hydrochloride | 200 mg |
| | Microcrystalline cellulose (Avicel PH101) | 130 mg |
| | Hydroxypropyl cellulose, Lo-sub, (LHPC, LH11) | 99 mg |
| | Sodium starch glycollate (Explotab) | 30 mg |
| | Povidone K30 | 36 mg |
| | Magnesium Stearate | 5 mg |
| | Compression weight | 1000 mg |
| | Coating: | |
| | Polymer dispersion (Hydroxypropylmethylcellulose and titanium dioxide and polyethylene glycol 400 and colourant) | 20 mg |
| | Polishing: | |
| | Polyethylene glycol 8000 | 2 mg |
| | Total weight | 1022 mg |
| B. | Dispersible film-coated tablet | |
| | Core: | |
| | Compound of Example 1 | 500 mg |
| | Proguanil hydrochloride | 200 mg |
| | Microcrystalline cellulose (Avicel PH101) | 100 mg |
| | Hydroxypropyl cellulose, Lo-sub, (LHPC, LH11) | 83 mg |
| | Sodium starch glycollate (Explotab) | 40 mg |

-continued

| | |
|---|---:|
| Povidone K30 | 20 mg |
| Magnesium stearate | 5 mg |
| Sodium docusate | 1 mg |
| Magnesium aluminium silicate (Veegum F) | 50 mg |
| Sodium saccharin | 1 mg |
| Compression weight | 1000 mg |
| Coating: | |
| Polymer dispersion (Hydroxypropylmethylcellulose and titanium dioxide and polyethylene glycol 400 and colourant) | 10 mg |
| Polishing: | |
| Polyethylene glycol 8000 | 2 mg |
| Total weight | 1012 mg |

Biological Test Results

EXAMPLE 3

Comparison of drug interactions in combinations of compound of Example 1 with other antimalarials.

In vitro drug sensitivity studies were carried out using the semiautomated technique of Desjardins (Desjardins et. al. Antimalarial Agents and Chemotherapy 1979; 16(6):710–718). Antimalarial activity in this system is assessed by inhibition of radiolabelled hypoxanthine incorporation into parasites by graded concentrations of drugs.

The antimalarial drugs for testing were dissolved in water, 95% ethanol, or DMSO; drugs dissolved in water were diluted 1:1 with 95% ethanol and drugs dissolved in ethanol were diluted 1:1 with water. Drug solutions were then diluted with culture medium containing 10% human serum to starting concentrations 20–50 times the estimated $IC_{50}$. The drugs tested and their solvents are listed below:

| Drug | Initial Solvent | Medium |
|---|---|---|
| Compound of Example 1 | DMSO | 1640 |
| Quinine | Ethanol-Water | 1640 |
| Chloroquine | Water-Ethanol | 1640 |
| Mefloquine | Ethanol-Water | 1640 |
| Primaquine | Ethanol-Water | 1640 |
| Artesunate | Ethanol-Water | 1640 |
| PM443 | DMSO | 1640 |
| Tetracycline | DMSO | 1640 |
| Norfloxacin | DMSO | 1640 |
| Ciprofloxacin | DMSO | 1640 |
| Proguanil | Ethanol-Water | Lo-folate |
| Cycloguanil | Ethanol-Water | Lo-folate |
| Pyrimethamine | DMSO | Lo-folate |
| Trimethoprim | DMSO | Lo-folate |
| Sulfamethoxazole | DMSO | Lo-folate |
| Dapsone | DMSO | Lo-folate |
| Clopidol | DMSO | Lo-folate |
| Allopurinol | Ethanol-Water | Lo-folate |
| PS-15 | DMSO | Lo-folate |
| WR99210 | DMSO | Lo-folate |

In order to study drug combinations, drug solutions at starting concentrations were combined in various ratios and 1:5,1:2,2:1 and 5:1). Drug solutions and combinations were then introduced into a 96-well microtitre plate to give duplicate rows of compound of example 1, the drug being combined and four combinations of the two drugs. Serial 1:3 dilutions of the drugs with media were made to fill the 96-well microtitre plate using a 12-channel pipetter. To evaluate drugs classified as dihydrofolic acid reductase (DHFR) inhibitors, modified culture medium was used which contained only physiologic concentrations of folic acid and PABA.

The remaining biological procedures were carried out according to the Desjardins technique except that three strains of P. falciparum were used (the multi-drug resistant W-2 clone, the drug-sensitive but melfloquine resistant D-6 clone and the C2B isolate resistant to the compound of example 1) and incubation was extended for 72 hours.

Individual $IC_{50}$s were calculated using the "MINSQ" program from Micromath Scientific Software. Each set of paired data was fitted to the hyperbolic tangent function used by Desjardins.

The $IC_{50}$s were normalised by assigning values of 1 to the $IC_{50}$ for the compound of Example 1 and to the other drug being combined with proportional normalised values for each ratio of the two drugs being studied. An isobologram was constructed by fitting the data to the equation:

$$Y1-[X_i/(X_i+e^{I}*(1-X_i))]$$

where $Y_i$=$IC_{50}$ for compound of compound of Example 1 when combined with

X=$IC_{50}$ for another drug when combined with compound of Example 1

I=interaction parameter indicating degree of reversal

Values of 1 were calculated for each combination. Positive values of I indicated a synergistic combination, negative values indicated antagonism and I=O indicated additive interaction.

The results are shown in Table 1.

TABLE 1

| Drug combined with compound of Example 1 | I | | |
|---|---|---|---|
| | W-2 | D-6 | C2B |
| Quinine | −1.36 | | |
| Chloroquine | −1.84 | −1.40 | |
| Mefloquine | −1.19 | | |
| Tetracycline | 1.27 | 1.11 | 0.02, −0.08 |
| Primaquine | −0.79 | | |
| Artesunic acid | | −0.18 | |
| PM443 | | −1.28 | |
| Norfloxacin | 1.02 | | |
| Ciprofloxacin | −1.22 | | |
| Pyrimethamine | 0.36 | | −0.48 |
| Trimethoprim | 1.27 | | 0.58 |
| Proguanil | 2.43, 2.88 | 2.56 | 2.56 |
| Cycloguanil | 2.21 | 1.66 | 0.13, −0.73 |
| Allopurinol | 1.14 | 0.43 | |
| PS-15 | 1.77, 0.65, 1.97 | −0.74 | |
| WR99210 | 0.02 | | |
| Sulfamethoxazole | 2.75 | | |
| Dapsone | −0.39 | | |
| Clopidol | 2.38, 2.65 | 0.73 | |

The results show that combinations of 2-[4-(4-chlorophenyl)cyclohexyl]-3-hydroxy-1,4-naphthoquinone and proguanil exhibited most consistent potentiation compared to the other drug combinations tested, particularly against the hydroxynaphthoquinone resistant C2B strain.

The optimum ratio of the combination with proguanil was estimated for each of the three strains of malaria parasite by determining the ratio of the $IC_{50}$ of proguanil to the $IC_{50}$ of the compound of Formula (II). The results are given in Table 2 below.

TABLE 2

|  | W-2 | D-6 | C2B |
|---|---|---|---|
| Proguanil: Compound of Formula (I) | 920:1<br>2473:1 | 4038:1 | 0.2:1 |

EXAMPLE 4

Comparison of anti-Toxoplasma activities in vivo of compound of Example 1, proguanil and combinations thereof Activities of the compounds and combinations were examined in a mouse model of *T. gondii*, using the increase in time to death and percent survival of the mice as measures of drug activity.

Groups of 10, 20 gm CBA/CA mice were infected orally by gavage with 6 cysts of the $C_{56}$ strain of *T. gondii* and drug treatment was started 3 days later and continued for 10 day. All drugs were administered orally by gavage. The following groups were examined:

Controls
Atovaquone@10 mg/kg
Atovaquone@25 mg/kg
Proguanil@25 mg/kg
Atovaquone@10 mg/kg+Proguanil@25 mg/kg
Atovaquone@25 mg/kg+Proguanil@25 mg/kg All animals were examined twice daily for 30 days and all deaths recorded.

The results are shown in Tables 3 and 4:

TABLE 3

| | | Mean Time to Death (days) | | |
|---|---|---|---|---|
| | | | Atovaquone | |
| | | 0 | 10 mg/kg | 25 mg/kg |
| Proguanil | 0 | 140 | 20.1 | 24.1 |
| (mg/kg) | 25 | 9.0 | 18.4 | 29.3 |

TABLE 4

| | | % Survival | | |
|---|---|---|---|---|
| | | | Atovaquone | |
| | | 0 | 10 mg/kg | 25 mg/kg |
| Proguanil | 0 | 10.0 | 10.1 | 10.0 |
| (mg/kg) | 25 | 0.0 | 0.0 | 80.0 |

The mean time to death of the control mice was 14 days, with only one animal surviving [10%] (This animal may not have become infected with the low inocculum used). Atovaquone alone increased this to 20.1 days at 10 mg/kg and 24.1 days at 25 mg/kg, in both cases with a single survivor [10%]. Proguanil, despite its excellent safety record in man, is toxic to mice. At 25 mg/kg, proguanil exhibits signs of toxicity, reducing the mean time to death to 9 days, with no survivors. The combination of 10 mg/kg atovaquone with 25 mg/kg proguanil gave a mean time to death of 18.4 days. The combination of 25 mg/kg atovaquone and 25 mg/kg proguanil gave an increased time to death in spite of the toxicity of proguanil and 80% of the mice survived compared to the minimal survival of 10% mice given atovaquone alone.

EXAMPLE 5

Comparison of anti-Toxoplasma activities in vitro of compound of Example 1, proguanil and combinations thereof In vivo drug sensitivity studies were carried out using a semi-automated technique based on that used for malaria (Desjardins et al, Antimicrobial Agents and Chemotherapy 1979 16 (6) 710–718), but utilising the selective incorporation of $^3$[H]-uracil by *T. gondii*. Antitoxoplasma activity in the system is assessed by inhibition of uptake of radiolabelled uracil into parasites by graded concentrations of drugs.

The drugs were dissolved in DMSO and dilution prepared using culture medium containing 3% foetal calf serum. To study drug combinations, drug solutions at starting concentrations were combined in various ratios 1:1, 1:3, 3:1. Serial 1:2 dilutions of the drug solutions and combinations were prepared and used in duplicate wells of a 96 well plate previously seeded with HeLa cells and RH strain *T. gondii*. Drugs were added two hours after the parasite and the plates incubated at 37° C. for 24 hours when the 3[H]-uracil was added and incubation continued for a further 8 hours. The assay was completed by removing the supernatant fluid, disrupting the *T .gondii* containing cells in SDS, and precipitating the labeled proteins with TCA onto filter mats. The incorporation of label was measured on a Beta plate scintillation counter. Percent inhibition of uracil incorporation was calculated for the compounds and combinations and $IC_{50}$s calculated using the GSI programme. $IC_{50}$s were normalised by assigning values of 1 to $IC_{50}$ for the compound of example 1 and proguanil with normalised values for each ratio of be two drugs being studied. An isobologram was constructed by plotting these normalised $IC_{50}$s against each other. Potentiation was indicated by the values occurring below the line of the isobologram, an additive effect by values on the line and antagonism by values above the line.

Plates mere set up in triplicate and all values plotted.

The results are shown in Table 5.

TABLE 5

| Normalised $IC_{50}$s | | |
|---|---|---|
| Atovaquone | Proguanil | Potentiation |
| 0.559278 | 0.583893 | No |
| 0.196689 | 0.614094 | Yes |
| 0.729381 | 0.253691 | Yes |
| 0.345238 | 0.527273 | Yes |
| 0.130952 | 0.6 | Yes |
| 0.233333 | 0.118182 | Yes |
| 0.404959 | 0.451538 | Yes |
| 0.229201 | 0.768462 | Yes |
| 0.244904 | 0.091538 | Yes |

The results show that combinations of atovaquone and proguanil exhibit potentiation in vitro against *T. gondii*.

EXAMPLE 6

Comparison of anti-Pneumocystis activities in vivo of compound of Example 1 proguanil and combinations thereof Activities of the compounds and combinations were examined in a scid mouse model of *Pneumocystis pneumonia*.

The level of infection of mice in each group was measured using standard lung impression smears and immunofluorescence tests. A score was assigned to each mouse where 0=no infection and +4=very heavy infection. The results are shown in Table 6.

TABLE 6

| Treatment | SCORE 0 | +1 | +3 | +4 | +4 | No. Infected/ No. Examined | Mean Score ±SE | % of Control |
|---|---|---|---|---|---|---|---|---|
| Control untreated | 0 | 0 | 0 | 3 | 7 | 10/10 | 3.70 ± 0.14 | 100 |
| Atovaquone 50 mg/kg p.o. daily | 0 | 0 | 5 | 5 | 0 | 10/10 | 2.50 ± 0.16 | 68 |
| Atovaquone 25 mg/kg p.o. daily | 0 | 0 | 1 | 7 | 2 | 10/10 | 3.10 ± 0.17 | 84 |
| Proguanil 25 mg/kg p.o. daily | 0 | 0 | 0 | 2 | 8 | 10/10 | 3.80 ± 0.13 | 85 |
| Atovaquone & Proguanil 50 + 25 mg/kg p.o daily | 5 | 4 | 1 | 0 | 0 | 5/10 | 0.50 ± 0.21 | 14 |
| Atovaquone & Proguanil 25 + 25 mg/kg p.o. daily | 1 | 0 | 4 | 4 | 0 | 8/9 | 2.22 ± 0.31 | 60 |

When dosed alone, atovaquone gave reductions in the infection score. Proguanil alone at 25 mg/kg/day was ineffective in prophylaxis of PCP in the scid mouse. Proguanil in combination with atovaquone showed synergy.

What is claimed is:

1. A method for the prophylaxis of malaria in mammals which comprises administering 2-[4-(4-chlorophenyl)cyclohexyl]-3-hydroxy-1,4-naphthoquinone and 1-(4-chlorophenyl)-5-isopropylbiguanide hydrochloride in a ratio of 1:1 to 3:1.

2. A method for the prophylaxis of malaria in mammals which comprises administering 2-[4-(4-chlorophenyl)cyclohexyl]-3-hydroxy-1,4-naphthoquinone and 1-(4-chlorophenyl)-5-isopropylbiguanide hydrochloride in a ratio of 5:2.

3. A method according to claim 1 or claim 2 wherein 2-[4-(4chlorophenyl)cyclohexyl]-3-hydroxy-1,4-naphthoquinone is administered either concomitantly or sequentially with 1-(4-chlorophenyl)-5-isopropylbiguanide hydrochloride.

4. A method according to claim 1 or claim 3 wherein 2-[4-(4-chlorophenyl)cyclohexyl]-3-hydroxy-1,4-naphthoquinone and 1-(4-chlorophenyl)-5-isopropylbiguanide hydrochloride is administered concomitantly and in a single composition.

5. A method according to claim 1 or claim 2 wherein the 2-[4-(4-chlorophenyl)cyclohexyl]-3-hydroxy-1,4-naphthoquinone is in the form of the trans isomer or a mixture of the cis and trans isomers in which the trans isomer predominates.

* * * * *